US008166834B2

(12) United States Patent
Dougherty, Jr. et al.

(10) Patent No.: US 8,166,834 B2
(45) Date of Patent: May 1, 2012

(54) IN-VITRO MEASUREMENT OF CATAMENIAL TAMPON SYSTEMS

(75) Inventors: Eugene Dougherty, Jr., Camden-Wyoming, DE (US); Keith Edgett, Middletown, DE (US); Scott Salmon, Tenafly, NJ (US); Mario Turchi, Tenafly, NJ (US); Phillip Ebert, Camden-Wyoming, DE (US); Robert Jorgensen, Middletown, DE (US); Steven O. Bordley, Dover, DE (US)

(73) Assignee: Playtex Products, LLC, Shelton, CT (US)

( * ) Notice: Subject to any disclaimer, the term of this patent is extended or adjusted under 35 U.S.C. 154(b) by 1349 days.

(21) Appl. No.: 11/821,338

(22) Filed: Jun. 21, 2007

(65) Prior Publication Data

US 2008/0319273 A1    Dec. 25, 2008

(51) Int. Cl.
*G01N 15/00* (2006.01)
*G01N 3/08* (2006.01)
*A61F 13/20* (2006.01)

(52) U.S. Cl. ........................................ 73/865.5; 604/11
(58) Field of Classification Search ........................ None
See application file for complete search history.

(56) References Cited

U.S. PATENT DOCUMENTS

| 4,239,043 A | 12/1980 | Gellert |
| 4,575,376 A | 3/1986 | Shah et al. |
| 5,659,934 A | 8/1997 | Jessup et al. |
| 7,166,085 B2 * | 1/2007 | Gann et al. .............. 604/11 |
| 2005/0273035 A1 * | 12/2005 | Gann et al. .............. 604/11 |
| 2006/0235361 A1 | 10/2006 | Agyapong et al. |

OTHER PUBLICATIONS

PCT International Search Report, International Application No. PCT/US2008/064937, International Filing Date May 28, 2008.
C. Rubod et al., A Biomechanical Model of the Pelvic Cavity: First Steps, Proceedings of the 28th IEEE, EMBS Annual International Conference, New York City, USA, Aug. 30-Sep. 3, 2006, pp. 968-971.
G.W. Rapp et al., A Comparison of the Absorptive Efficiency of Commercial Catamenial Tampons, pp. 1, 4, 8 and 14.

* cited by examiner

*Primary Examiner* — Hezron E Williams
*Assistant Examiner* — Mark A Shabman
(74) *Attorney, Agent, or Firm* — Michaud-Kinney Group LLP

(57) ABSTRACT

An apparatus for testing of medical products such as a feminine hygiene product, is presented. The apparatus includes a body, a pump and a vaginal canal assembly. The body includes an internal chamber and a bottom surface having a bore open to the internal chamber. The pump provides a fluid to the body. In one embodiment, the fluid is a menses simulant. The vaginal canal assembly includes an interior canal accepting the product. The vaginal canal assembly includes a passage providing the fluid to the interior canal. The apparatus includes a pressure regulator controlling pressure exerted on the vaginal canal assembly from a volume of air within the internal chamber. The apparatus includes a stand. The stand includes a retaining device and a locking device. The locking device cooperates with the retaining device to selectively secure the body in at least one of a rotational position and an angular position.

15 Claims, 11 Drawing Sheets

IN-VITRO MEASUREMENT OF CATAMENIAL TAMPON SYSTEMS

FIELD OF THE INVENTION

This invention relates generally to diagnostic instruments and, more particularly, to systems and methods for performing in-vitro testing of feminine hygiene products such as, for example, catamenial tampon systems.

Description of the Related Art

Generally speaking, it is useful in the development of medical and health care products to have an understanding of the biomechanical properties of tissues and organs of the human body. For example, it would be useful to have a simulator to model the biomechanical response of tissues and organs to a product aids in the design of a safe, comfortable and more efficient product. Modeling is particularly useful when the product is used internally within the human body such as, for example, when the product is a catamenial tampon system.

As can be appreciated, it is easier to measure and model the biomechanical properties of external tissues and organs as opposed to internal tissues and organs, which are typically harder to access and therefore measure. For example, the human female vagina is located in the lower pelvic cavity and is surrounded by organs such as the uterus, the bladder, and the rectum. The vagina is a collapsed tube-like structure composed of fibromuscular tissue layers. The vaginal walls are suspended and attached to paravaginal connective tissues. The vaginal walls are also connected to the lateral pelvic floor by connective tissues and smooth muscle layers, which allow the vagina to deform and be displaced. For example, the degree of vaginal tissue deformation is significantly influenced by the biomechanical properties of surrounding organs and tissues as well as the fact that there is no rigid supporting structure around the vagina. As a result of the anatomical complexities of the vagina and interaction of surrounding tissues and organs, there has been little success in accurately measuring and modeling the anatomical and biomechanical properties of the vagina.

Product testing such as, for example, tampon testing, is typically performed in-vivo with a number of panelists using various tampon configurations and testing personnel employing imaging (such as magnetic resonance imaging (MRI)) of the pelvic regional to view internal organs, bone structure, muscle and other tissue, fluid (e.g. blood), and their interaction with products of interest. With the MRI images of a tampon in the vagina, performance characteristics of the tampon may be evaluated. However, testing in this fashion (e.g., using panelist and MRI imaging) can be costly and limited as minor improvements to a product made after the initial test can not be re-tested without organizing subjects for additional in-vivo testing. Alternatively, a testing regime used in the industry to provide consumers with a standard indication of tampon absorbency is a U.S. Food and Drug Administration (FDA) syngyna (simulated vaginal) test, entitled "A Comparison of Absorptive Efficiency of Commercial Catamenial Tampons", available on the World Wide Web at "http://www.mum.org/syngyna2.htm." As its name implies, the syngyna test method is conducted using a simulated vagina. While the syngyna test may be useful for regulatory purposes, the inventors have discovered perceived deficiencies in the testing regime at least since the syngyna test is not based on an anatomically correct human female vagina.

Accordingly, the inventors have discovered that there is a need for improved instruments and procedures for testing medical devices such as, for example, catamenial tampons. There is also a need for systems and methods for accurately portraying the anatomical and biomechanical properties of internal tissues and organs to provide in-vitro testing, for example, testing in a laboratory setting, to improve response time and to permit faster development of product improvements.

SUMMARY OF THE INVENTION

The present invention is directed to an apparatus for in-vitro testing of medical devices and, in particular, feminine hygiene products. The apparatus includes a body, a pump and a vaginal canal assembly. The body includes an internal chamber and a bottom surface having a central bore open to the internal chamber. The pump is coupled to the body and provides a fluid of interest. In one embodiment, the fluid of interest is a menses simulant. The vaginal canal assembly is located within the internal chamber of the body. The vaginal canal assembly includes a wall defining an interior canal. The interior canal has an open end and a closed end. When located in the internal chamber, the open end of the interior canal is coaxial with the central bore of the bottom surface. The interior canal accepts the feminine hygiene product for testing. The vaginal canal assembly also includes a passage in the wall for providing the fluid to the interior canal during testing.

In one embodiment, the vaginal canal assembly further includes a retaining plate portion. When the vaginal canal assembly is disposed in the body, the retaining plate portion seals the central bore. In one embodiment, the testing apparatus further includes a pressure regulator that couples the body to an air supply. The pressure regulator controls pressure exerted on the vaginal canal assembly from a volume of air within the internal chamber. In on embodiment, the internal chamber of the body can be filled with water or gel to simulate overall pressures of surrounding anatomical features exerted on the vaginal canal assembly. The pressure of the water or gel can also be augmented and/or adjusted with pressurized air from the pressure regulator.

In one embodiment, the testing apparatus includes a retaining ring located about an external surface of the vaginal canal assembly. The retaining ring and the retaining plate portion of the vaginal canal assembly cooperating to seal the central bore of the body.

In another embodiment, the testing apparatus includes a stand supporting the body. The stand includes a retaining device and a locking device. The retaining device rotationally and angularly couples the body to the stand. The locking device cooperates with the retaining device to selectively secure the body in at least one of a rotational position and an angular position.

In yet another embodiment, the testing apparatus includes a bracket assembly located within the internal chamber. The bracket assembly has upright portions. The upright portions accept the vaginal canal assembly and retain the vaginal canal assembly at a predetermined orientation within the internal chamber. In one embodiment, the bracket assembly further includes a pin, and the upright portions include a set of opposing bores aligned along a vertical portion of the upright portions. The opposing bores accept the pin. An angular orientation of the vaginal canal assembly is selectively adjusted by positioning the pin within differing corresponding opposing bores.

In still another embodiment, the testing apparatus includes a bladder disposed in the chamber in proximity to the vaginal canal assembly. The bladder simulates a urinary bladder that exerts a force on the vaginal canal assembly.

In one aspect of the present invention, a method for forming a vaginal canal assembly of an in-vitro testing apparatus is presented. The method includes the steps of measuring a vaginal cavity of a subject human female, modeling the measured vaginal cavity in three-dimensional space, and molding the vaginal canal assembly from the three-dimensional model. In one embodiment, the measuring step includes imaging the subject human female's pelvic cavity. In one embodiment, the modeling step includes analyzing the imaging data by segmenting the pelvic cavity to identify the vaginal cavity and surrounding tissues and organs, and generating object boundaries in three-dimensional space for the vaginal cavity and the surrounding tissues and organs. In one embodiment, the molding step includes developing a mold assembly design from the generated object boundaries of the subject human female's pelvic cavity.

In another embodiment, the steps of measuring, modeling and molding are performed for a plurality of subject human females. The plurality of subject human females include females of varying ages including young adult, adult and senior citizens, and varying sizes including short, average and tall in height, and slim, average and heavy in weight.

BRIEF DESCRIPTION OF THE DRAWINGS

The features and advantages of the present invention will be better understood when the Detailed Description of the Preferred Embodiments given below is considered in conjunction with the figures provided.

In these figures like structures are assigned like reference numerals, but may not be referenced in the description of all figures.

DETAILED DESCRIPTION OF PREFERED EMBODIMENTS

In one aspect of the present invention an in-vitro testing apparatus is provided. The testing apparatus models the vaginal anatomy of a female human. As described herein, the testing apparatus simulates both of the anatomical and biomechanical properties of the vagina and surrounding tissues and organs to monitor and evaluate, in one embodiment, catamenial tampon performance and effectiveness. As should be appreciated the monitoring and evaluating of numerous tampon designs in a laboratory setting with a testing apparatus aids in the development of rapid product improvements. It should be appreciated that while the present application describes the inventive in-vitro testing apparatus used for testing tampon performance and effectiveness, the present invention is not limited in this regard. For example, the in-vitro testing apparatus may be employed anywhere that evaluation is needed that requires an anatomically and biomechanically accurate human female vagina.

As is generally known in the art, a catamenial tampon or tampon pledget is an absorbent structure that is inserted into a human vagina to absorb menses or other fluids. A tampon pledget is typically a cylindrical configuration having a length of about 30 to 60 mm and a width of about 8 to 20 mm. Characteristics that have been identified as factors that influence pledget performance include placement (e.g., position at which the tampon is located within the anatomy of the vagina), physical dimension of the pledget, pressure, lubricity, tissue elasticity, dynamic of body motion/activity during use (e.g., duration of activities such as jumping, running, laughing, couching, etc.), specifics of menstrual flow (e.g., light versus heavy flow volume), and interaction with adjacent tissues, organs and structures (e.g., colon, bladder, uterus, pelvis and coccyx).

Figure 1:
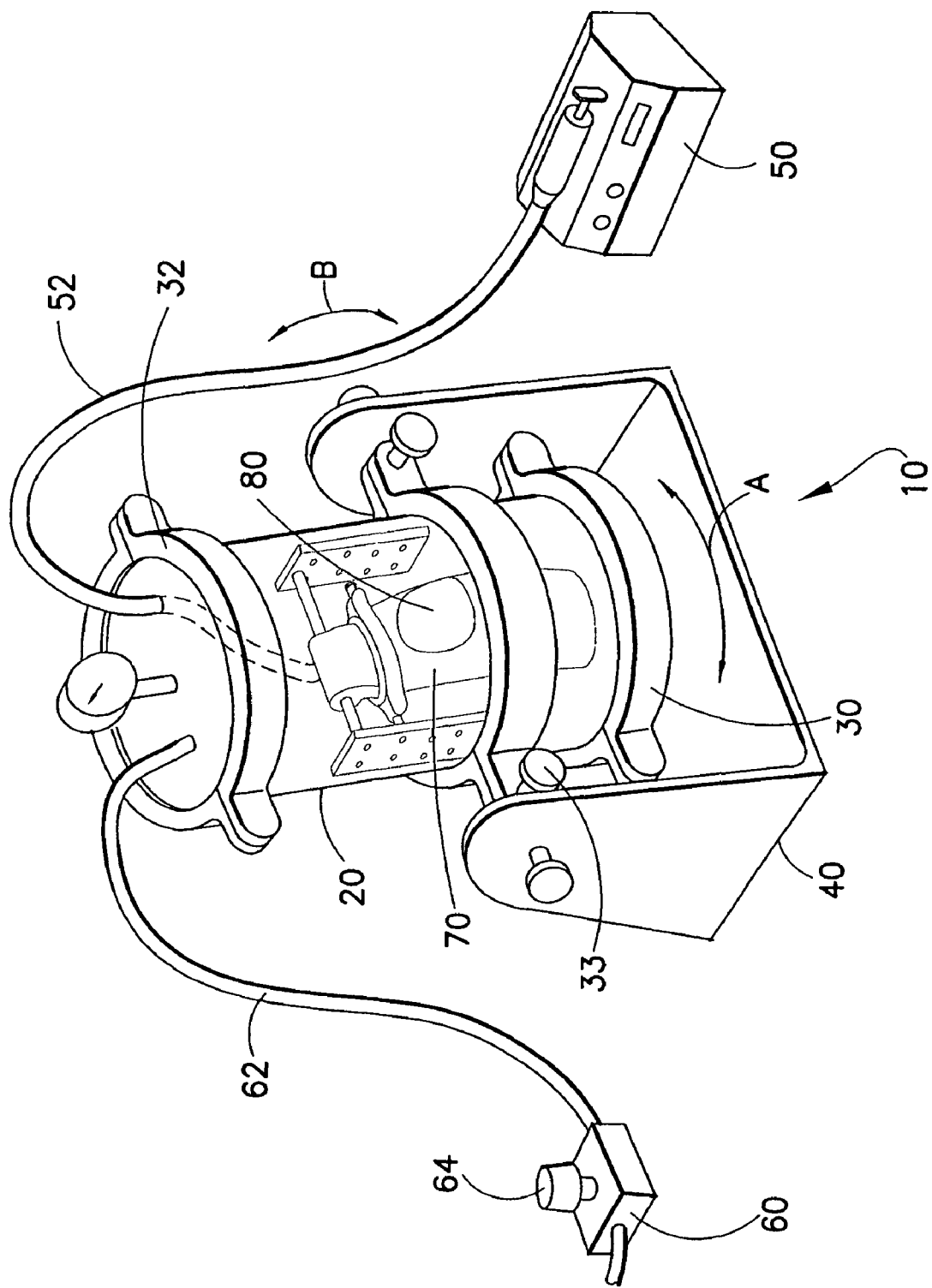
FIG. 1 is a perspective view of an apparatus for in-vitro testing of a feminine hygiene product configured and operating in accordance with one embodiment of the present invention.
Figure 2:
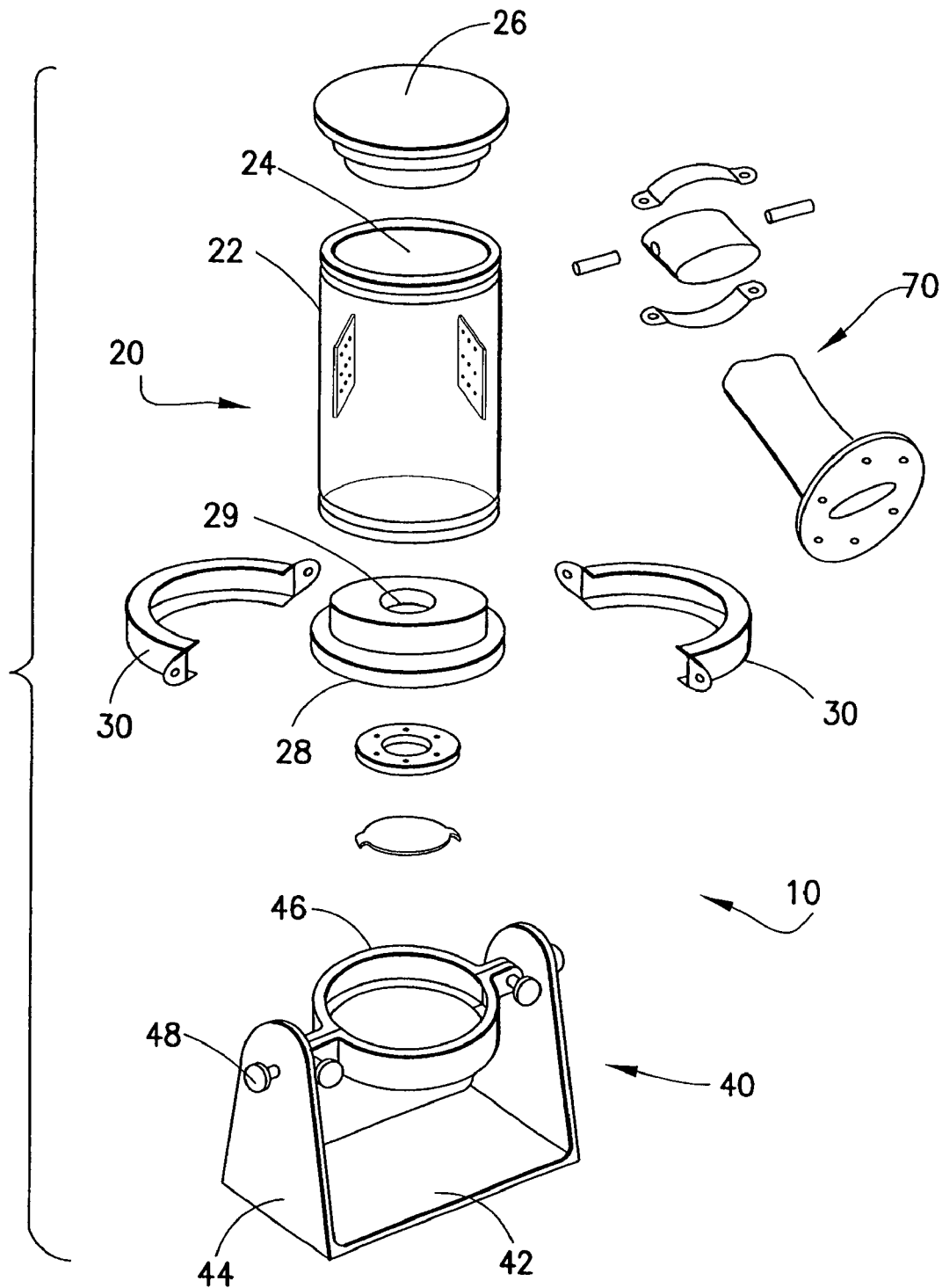
FIG. 2 is an exploded assembly view of the testing apparatus of FIG. 1.

FIGS. 1 and 2 illustrates a testing apparatus 10 configured and operating in accordance with one embodiment of the present invention to simulate, anatomically and biomechanically, a human vagina. As shown in FIGS. 1 and 2, the testing apparatus 10 includes a pressure vessel assembly 20, a vaginal canal assembly 70 disposed within the pressure vessel assembly 20, a stand 40 supporting the pressure vessel assembly 20, a pump 50 for delivering a fluid of interest such as, for example, menses simulant, and a pressure regulator 60.

In one embodiment, the pressure vessel assembly 20 includes a body portion 22 having a cylindrical shape and defining an internal cavity or chamber 24, a top cap 26, and a bottom cap 28. The top cap 26 and/or the bottom cap 28 are removably coupled to the body portion 22 by, for example, frictional or threaded attachment, as is generally known in the art. One or more of the top cap 26 and bottom cap 28 is removed to access the internal chamber 24 of the body portion 22. For example, access to the internal chamber 24 permits repositioning, maintenance and/or replacement of one or more components disposed in the internal chamber 24. In one embodiment, the body portion 22 is comprised of transparent material such as, for example, a clear polycarbonate, to allow observation of elements disposed within the body portion 22. In one embodiment, the bottom cap 28 includes a centrally located bore 29. In one embodiment, the top cap 26 and the bottom cap 28 are each secured about the pressure vessel assembly 20 with clamps 30 and 32, respectively. In one embodiment, the clamps 30 and 32 include split ring clamping devices or the like. The clamps 30 and 32 seal the chamber 24 such that a volume of the chamber 24 may be pressurized by filling the volume with a liquid or gas, as is described in detail below.

In accordance with one aspect of the present invention, the internal chamber 24 of the pressure vessel assembly 20 is large enough to contain a variety of profiles of the vaginal canal assembly 70. For example, and as is described in detail below, different profiles of the vaginal canal assembly 70 represent females of varying ages (e.g., young adult, adult and senior citizens) and sizes (e.g., short, average and tall in height, slim, average and heavy in weight). Moreover, the internal chamber 24 may also be sized to accommodate models of anatomical structures (e.g., organs and tissues) surrounding the vagina such as, for example, the uterus, the bladder, and the rectum. For example, FIG. 1 illustrates a model of a urinary bladder 80 disposed in the chamber 24 of the vessel assembly 20 in proximity to the vaginal canal assembly 70. In one embodiment, the bladder 80 has a capacity to hold a volume of about five hundred cubic centimeters (500 cc) of fluid to, for example, simulate a bladder full of urine.

As illustrated in FIG. 1, the pressure vessel assembly 20 is supported by the stand 40 so that the vessel assembly 20 rotates about a horizontal axis, shown generally by line A, and about a vertical axis, shown generally by line B. Referring again to FIGS. 1 and 2, in one embodiment, the stand 40 includes a base 42, at least one leg 44, a retaining device 46 for rotational coupling the pressure vessel assembly 20 to the stand 40 and a locking device 48 for securing the pressure vessel assembly 20 in a desired rotational or angular position relative to the horizontal and vertical axis, lines A and B, respectively. In one embodiment, the retaining device 46 includes a split ring clamping device or the like. It should be appreciated that the retaining device 46 and the locking device 48 cooperate such that the orientation of the pressure vessel assembly 20 and, importantly, the vaginal canal assembly 70 is angularly and rotationally adjustable to simulate body positions (e.g., a woman sitting down, lying down, standing up, and the like). In one embodiment, the angular and rotational adjustments permit an about 180° range of motion about the horizontal and vertical axis, lines A and B, respectively.

As shown in FIG. 1, the pump 50 delivers a fluid of interest to the vessel assembly 20 and, in particular, to the vaginal canal assembly 70 via a tube 52. In one embodiment, the pump 50 is a controllable, variable rate, metering pump that delivers, for example, either water, a syngyna fluid or a suitable menses simulant to the vaginal canal assembly 70 to simulate the cervical os. In one embodiment, a flow rate of the fluid of interest is within a range of about 0.06 to 2.2 ml per minute. In one embodiment, the pump 50 is a metering gland, positive displacement pump coupled with an associated pump controller having a Hall effect sensor (e.g., Model No. 1323359-ZZ1A of the IVEK Corporation, North Springfield, Vt. USA).

The pressure regulator 60 is also coupled to the vessel assembly 20 via a tube 62 for controlling a pressure within the chamber 24. It should be appreciated that by varying the pressure within the chamber 24, a magnitude of a compressive force exerted on the vaginal canal assembly 70 is adjusted (e.g., selectively increased or decreased). In varying the pressure within the chamber 24, inter and intra-vaginal pressures, as are known to those skilled in the art, are simulated. In one embodiment, operating ranges of static pressure within the chamber 24 and surrounding the vaginal canal assembly 70 extends from a range of about 0 to 20 psig (absolute pressure). In one embodiment, the pressure in the chamber 24 is adjusted using compressed air. It should be appreciated that the pressure regulator 60 includes means 64 for adjusting and measuring the pressure within the vessel assembly 20 and, importantly, in proximity to the vaginal canal assembly 70. For example, the pressure regulator 60 provides an ability to simulate pressure exerted on the vagina by a full urinary bladder such as the urinary bladder 80 shown in FIG. 1. In one embodiment, the pressure vessel assembly 20 includes an over-pressure relief device, as is known in the art, to ensure safe operation of the testing apparatus 10 under the aforementioned varying pressure conditions.

In one embodiment, the vagina canal assembly 70 is secured within the chamber 24 of the pressure vessel assembly 20 by a bracket assembly (described below). The bracket assembly permits positioning the vagina canal assembly 70 within the internal chamber 24 at a predetermined orientation. In one embodiment, the urinary bladder 90 is also affixed within chamber 24 by the bracket assembly such that a relative position of the vagina canal assembly 70 and the bladder 80 is controllable.

Figure 3:
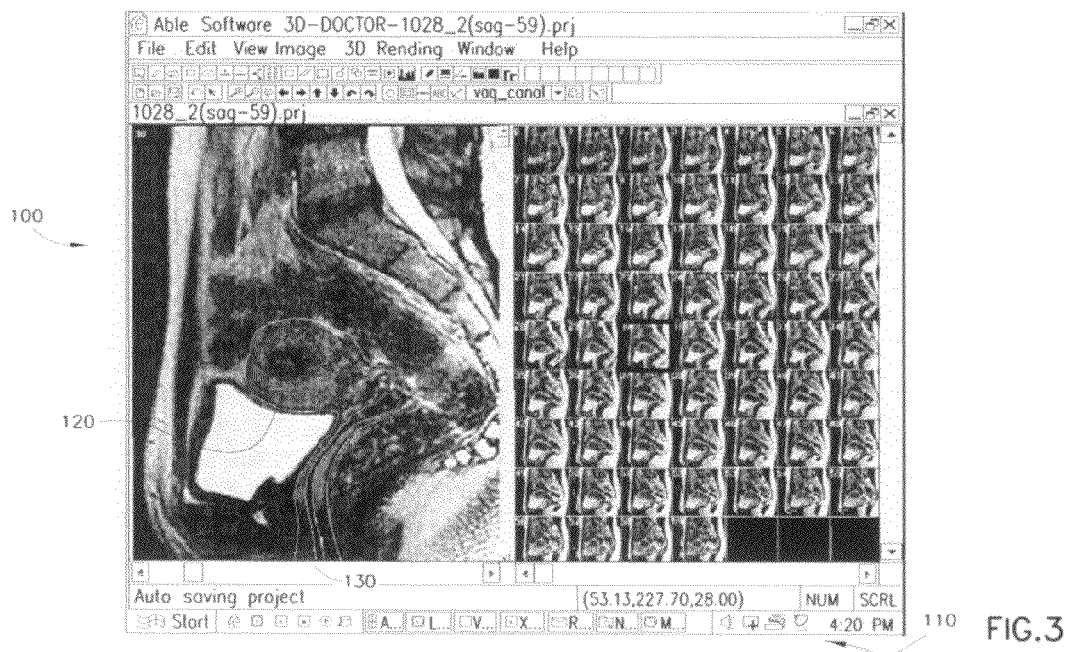
FIG. 3 is a graphical user interface view from a three-dimensional modeling program illustrating a subject female's pelvic cavity.

In accordance with one aspect of the present invention the configuration of the vagina canal assembly 70 correctly models the anatomical structure of a subject woman's vagina. In this respect, the subject woman's vaginal anatomy is measured, modeled and molded using, for example, computer aided design (CAD) analysis. In accordance with the present invention a magnetic resonance imaging (MRI) study (e.g., multiple MRI scans are taken) of a pelvic regional and, specifically, a vaginal cavity, of a subject woman is undertaken by the inventors or under the inventors' direction. The MRI data is analyzed by a three-dimensional software program (3-D software) to model the vaginal cavity. For example, the MRI data is inputted into the 3-D software and segmented by the software user such that the 3-D software provides a dimensionally accurate representation of the subject female's vaginal anatomy. In one embodiment, the 3-D software is 3D DOCTOR Medical Modeling and Imaging Software of Able Software, Corp., Lexington, Mass., USA. In one embodiment, the 3-D software is utilized to segment the vaginal cavity and surrounding organs and tissue of interest. The inventors have discovered that segmenting the vaginal cavity permits generation of accurate object boundaries and provides an anatomically correct three-dimensional computer aided design (e.g., 3D-CAD) file of the subject woman's vaginal anatomy. FIG. 3 illustrates a screen print of the 3-D software depicting a subject woman's pelvic region 100. As shown in FIG. 3, the 3-D software uses the MRI data to presents a plurality of images 110 of the pelvic region 100 representing the pelvic region viewed from various orientations. As shown in FIG. 3, a tracing function of the 3-D software is utilized to segment organs within the pelvic region 100, e.g., identify and segment the uterus 120 and vaginal cavity 130.

Figure 4A:
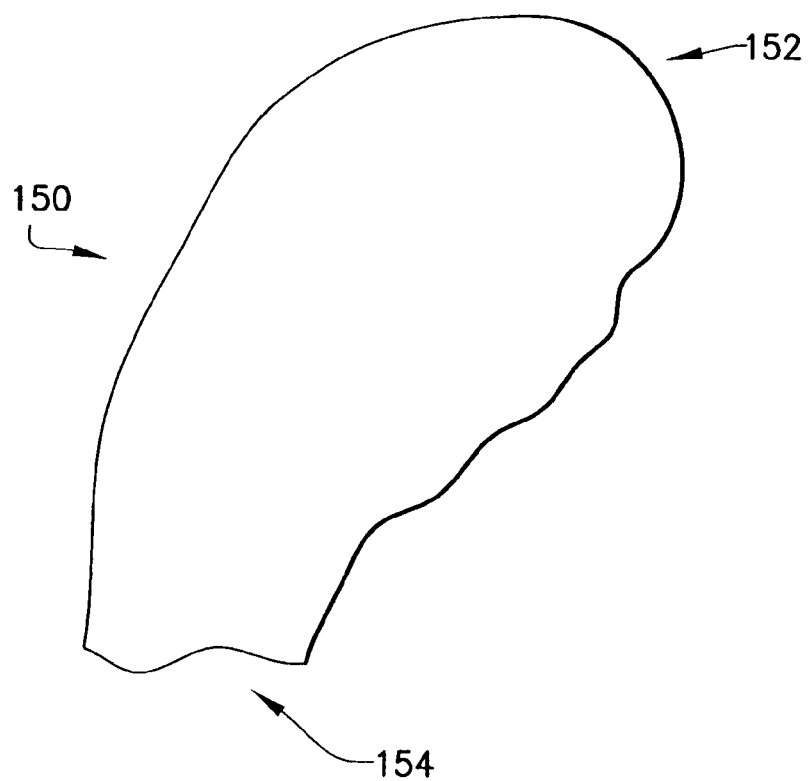
FIGS. 4A and 4B illustrate a molded vaginal canal assembly configured and operating in accordance with one embodiment of the present invention.
Figure 4B:
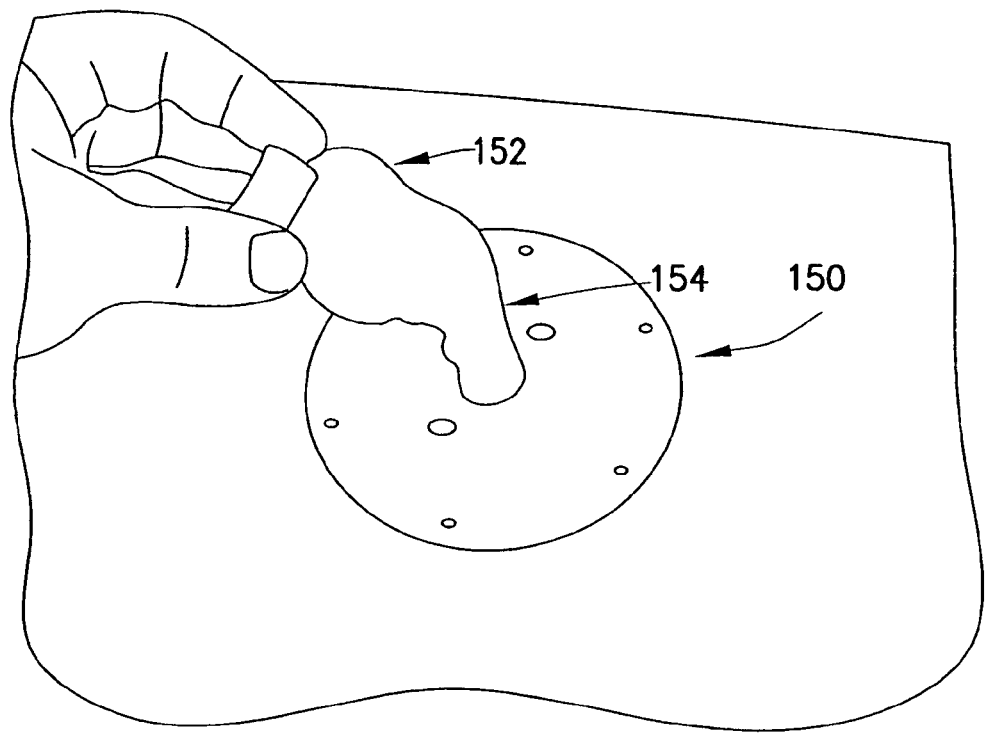
Figure 7:
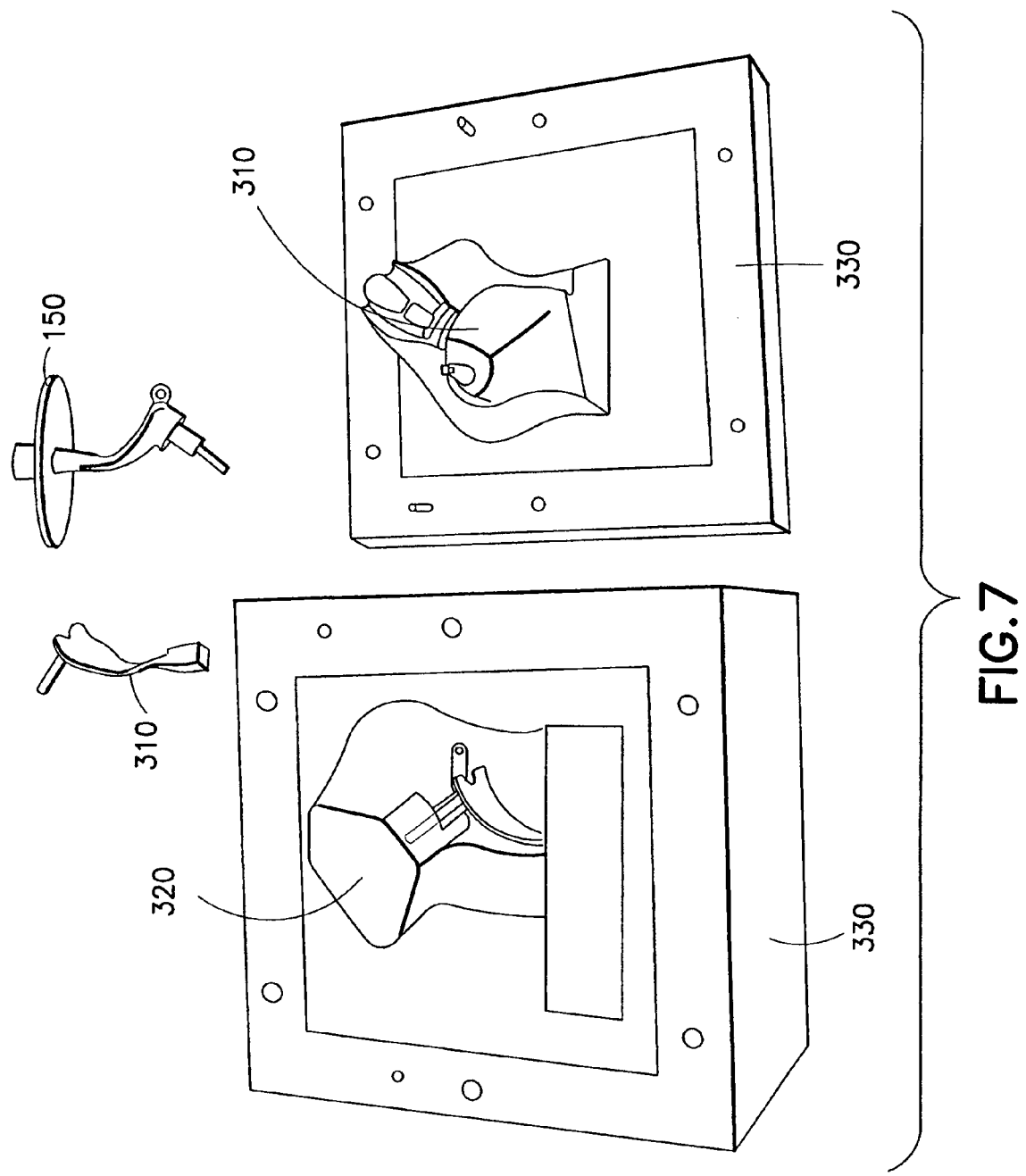
FIG. 7 illustrates a mold design assembly for molding the vaginal canal assembly of FIGS. 4A and 4B.

The inventors discovered that by providing the 3D-CAD file as input to conventional three-dimensional mold design software, an anatomically accurate mold assembly design is produced. In one embodiment, conventional three-dimensional mold design software includes PRO-ENGINEER software of Parametric Technology Corporation, Needham, Mass., USA, SOLIDWORKS software of SolidWorks Corporation, Concord, Mass., USA, and similar software. The output of the three-dimensional mold design software, e.g., the mold assembly design, is used to fabricate a mold assembly 300 including, for example, a mold core 310, cavity 320 and mold base 330, as is known in the art, and as illustrated in FIG. 7. For example, an electronic file including the mold assembly design is provided to suitable numerical control (NC) tooling to fabricate the mold to the required specifications of the mold assembly design. FIGS. 4A and 4B illustrate exterior views of a molded vaginal canal assembly 150 based upon the modeled vaginal cavity. The vaginal canal assembly 150 is fabricated in a mold assembly generated by the 3-D mold design software from the 3D-CAD file of the vaginal cavity. As shown in FIGS. 4A and 4B, the molded vaginal canal assembly 150 is somewhat flat and larger near a top portion 152, which would be closest to the uterus when viewed from within the female pelvic cavity, and smaller near a bottom portion 154, which would be at a vaginal introitus when viewed from within the pelvic cavity.

It should be appreciated that it is within the scope of the present invention to measure, model and mold, e.g., using the aforementioned 3-D software and 3-D mold design software, a plurality of female subjects to construct a plurality of different profiles of vaginal canal assemblies for use within the testing apparatus 10. For example, the above defined process for measuring, modeling and molding a subject woman's anatomy may be repeated for females of varying ages (e.g., young adult, adult and senior citizens) and sizes (e.g., short, average and tall in height, slim, average and heavy in weight). The plurality of molded vaginal canal assemblies provided by such an analysis are used interchangeable with the testing apparatus 10 to evaluate the effectiveness of various feminine hygiene products on a multitude of female subjects in a laboratory setting, as described herein.

Figure 8:
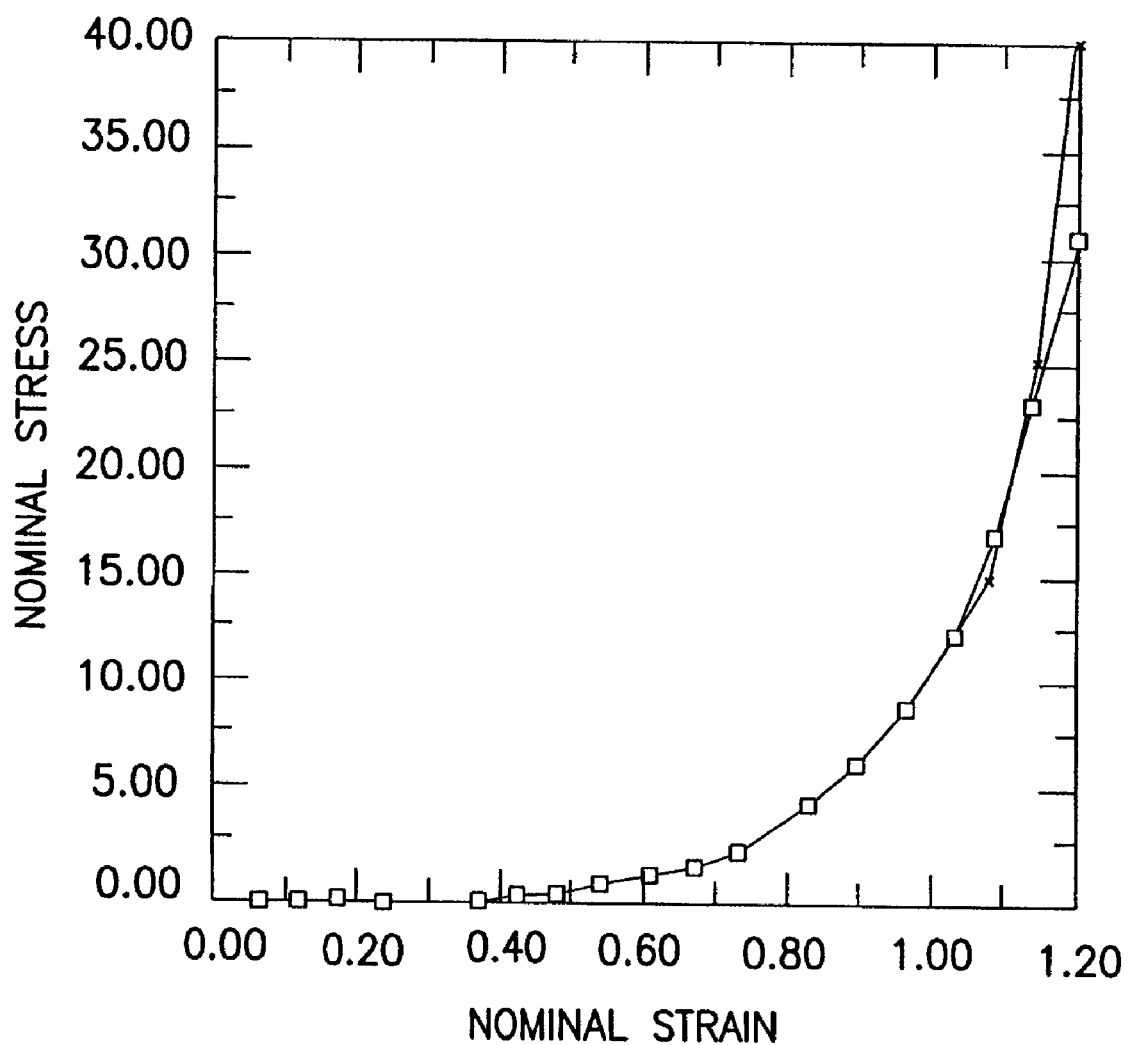
FIG. 8 depicts a vaginal wall stress-strain composite profile in accordance with one embodiment of the present invention.

It should also be appreciated that the molded vaginal canal assembly 150, having been modeled on a subject female's anatomy, is an accurate dimensional representation of the female's vaginal cavity. Additionally, it is also within the scope of the present invention to provide a model that accurately portrays the biomechanical properties of the female's vaginal cavity. As described above, each of the numerous tissues and organs of the female pelvic anatomy exert various biomechanical properties such as, for example, stress-strain profiles and surface properties, that influence the relative effectiveness of a product disposed and operating within the pelvic cavity. The prior art includes studies of biomechanical properties of the tissues and organs within the pelvic cavity. From such studies and independent analysis, the inventors have compiled a vaginal wall stress-strain composite profile, depicted in FIG. 8. The profile of FIG. 8 depicts the stress in grams per square millimeter (on the Y-axis) versus fractional strain (on the X-axis) for actual vaginal tissue, removed surgically from a woman's body and tested for its biomechanical properties. The data has also been fitted to a special semi-empirical model generally known to those skilled in the art as the Ogden hyperelastic material model. The data was found in the following reference: P.E.P. Petros and U. I. Ulmsten, "An Integral Theory and its Method for the Diagnosis and Management of Female Urinary Incontinence", Scandinavian Journal of Urology and Nephrology, Supplement No. 153.

From the composite profile the inventors identified materials that meet the profile (e.g., mimicked the stress-strain characteristics of the human vagina), that were moldable and castable, and that exhibited suitable wear (e.g., did not tear easily under everyday use). Accordingly, each component within the internal chamber 24 of the testing apparatus 10 is designed to simulate not only a dimensionally accurate anatomic structure of the female anatomy but also to simulate the biomechanical properties and surface properties of the organ and tissue that the component is modeling. For example, it is known in the art that the vaginal cavity is somewhat elastic. The elasticity is achieved in the vaginal canal assemblies 70 and 150 of the present invention by manufacturing the assembly out of, for example, an elastomer such as room-temperature vulcanizing (RTV) silicone rubber, castable polyurethane, rubber latex, plasticized polyvinyl chloride (PVC), styrene-butadiene and like castable materials. In one embodiment, the inventors have discovered that the elasticity of the vaginal canal assemblies 70 and 150 is such that a free state volume of the vaginal canal is significantly collapsed upon application of a hydrostatic pressure of about 0.3 psi (absolute). In one embodiment, the target hydrostatic pressure is obtained by filling the chamber 24 with water or another suitable liquid.

Figure 5A:
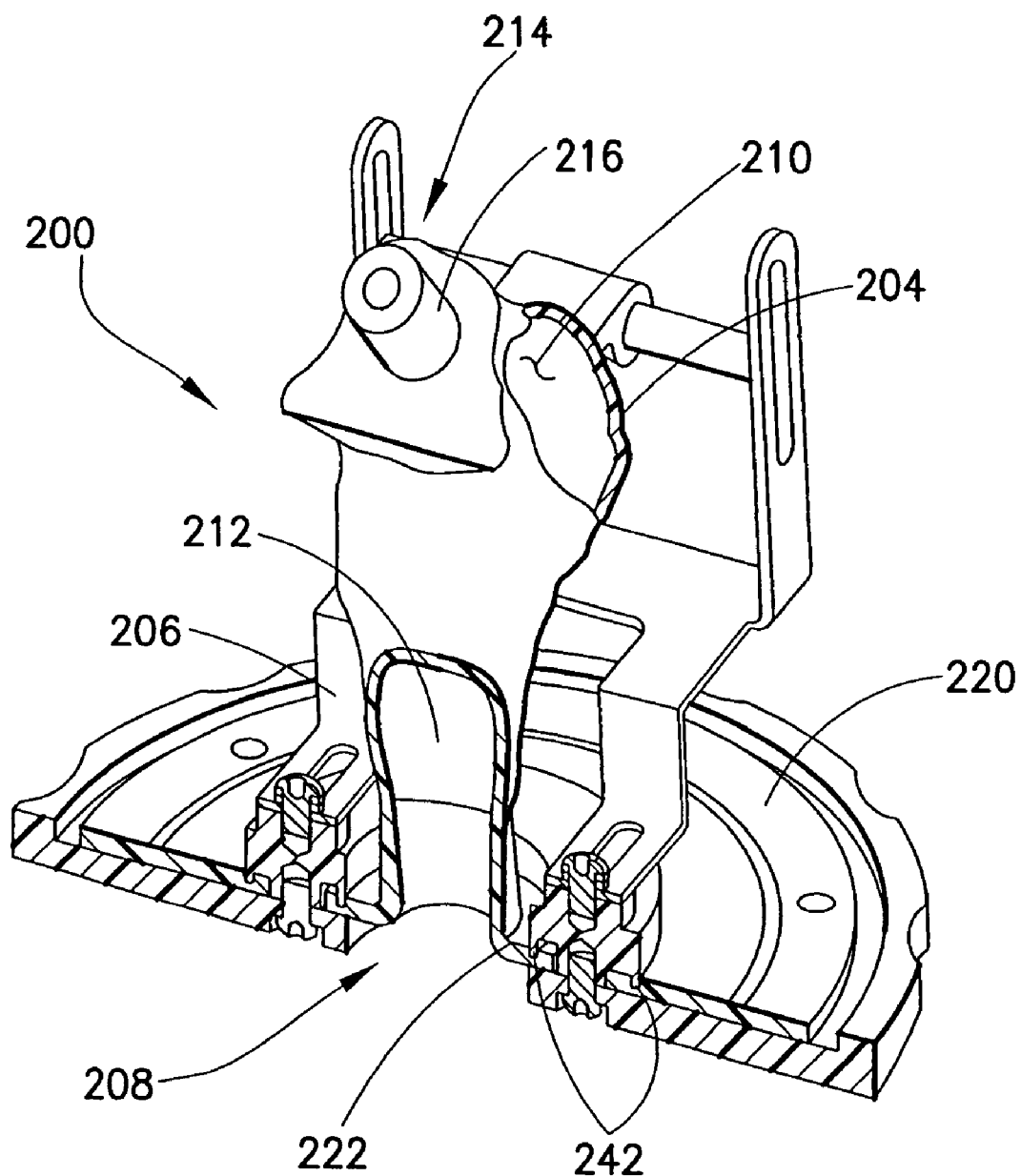
FIGS. 5A-5C illustrate the molded vaginal canal assembly assembled on a bottom portion of the testing apparatus of FIG. 1.
Figure 5B:
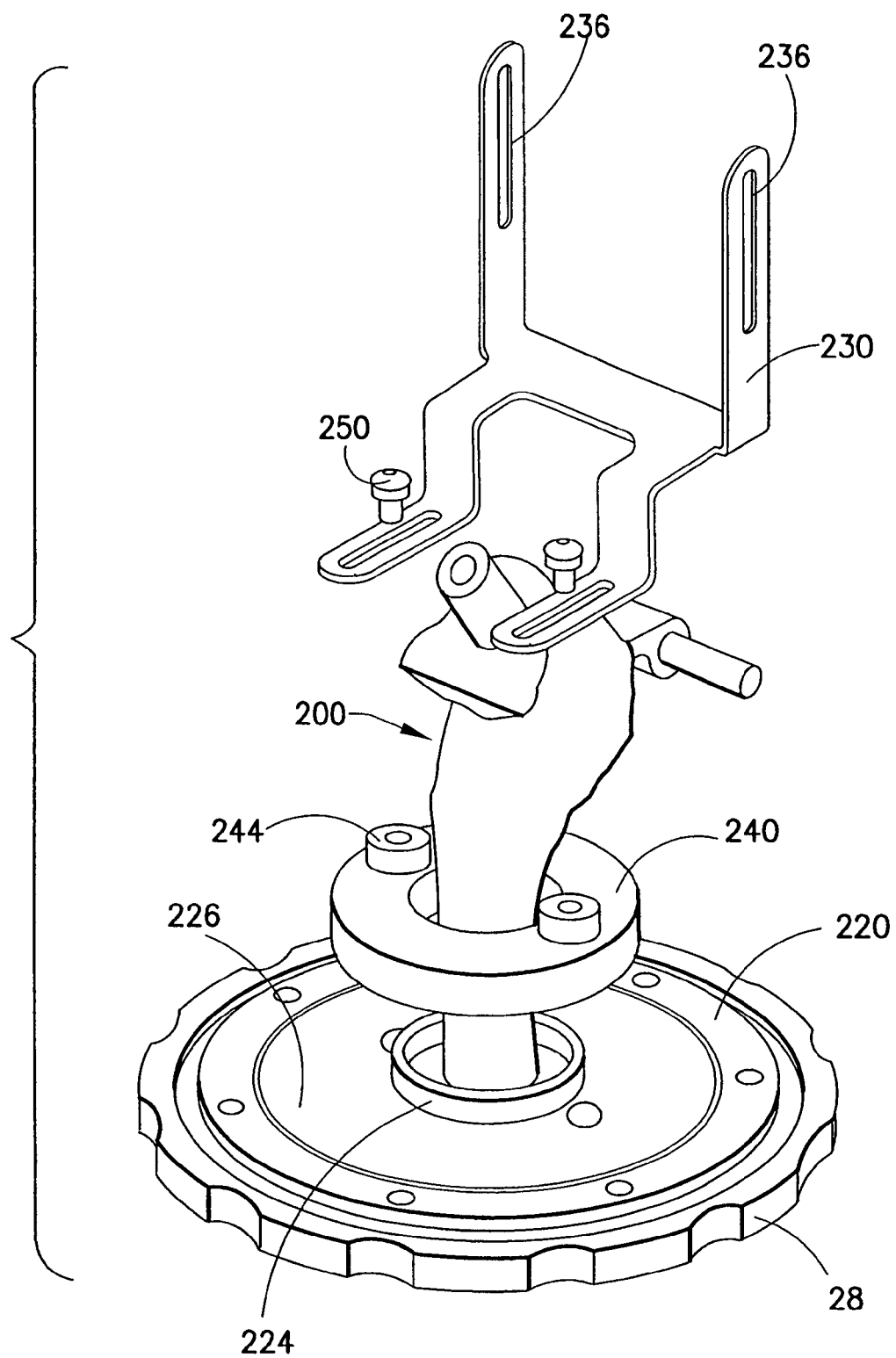
Figure 5C:
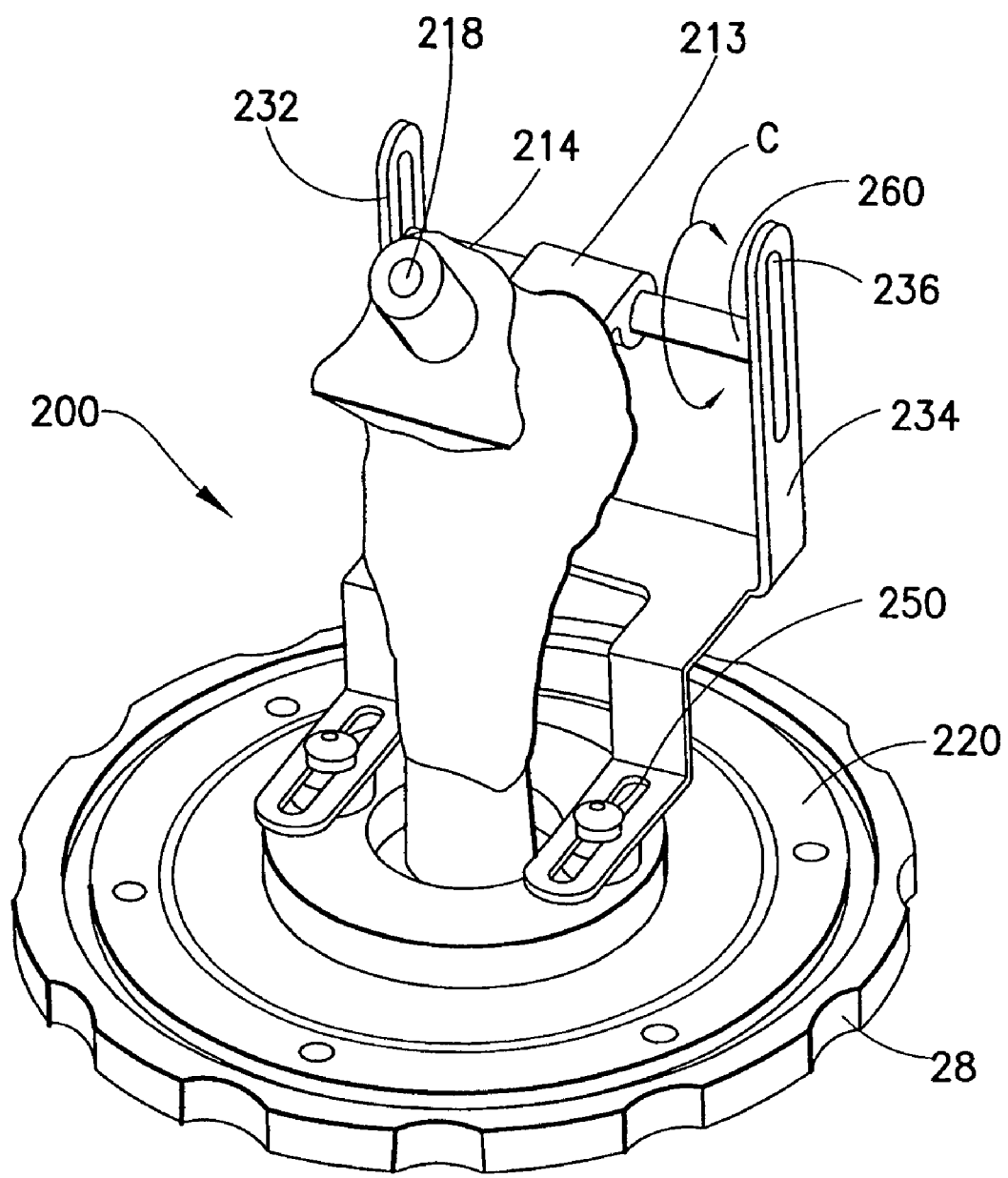

FIGS. 5A-5C illustrate a molded vaginal canal assembly 200 (substantially similar to assemblies 70 and 150) having an integrally formed retaining plate portion 220 coupled to a bracket assembly 230. As shown in FIG. 5A, the vaginal canal assembly 200 includes an exterior surface portion 202 and a wall 204 defining an interior canal 206 having an open end 208 and a closed end 210. The interior canal 206 simulates the vaginal cavity of the subject female, where the closed end 210 terminates at what within the human body is the cervix or lower portion of the uterus and the open end 208 simulates the vulva or external portion of the vagina. An intermediate portion 212 of the interior canal 206 simulates the vaginal passageway (e.g., the "birth canal"). The open end 208 of the vaginal canal assembly 200 terminates at the retaining plate portion 220. During testing, a product of interest (e.g., a tampon) is inserted into the interior canal 206.

As shown in FIGS. 5A-5C, the retaining plate portion 220 of the vaginal canal assembly 200 includes a central bore 222. In operation, the retaining plate portion 220 is disposed on the bottom cap 28 of the pressure vessel assembly 20 such that the central bore 222 of the retaining plate portion 220 is coaxial with the central bore 29 of the bottom cap 28. In one embodiment, the retaining plate portion 220 includes a retaining rib 224 (FIG. 5B) extending upwardly from a first surface 226 of the retaining plate portion 220, where the first surface 226 is located opposite the bottom cap 28. In one embodiment, the retaining rib 224 is of a diameter that is larger than the central bore 222 such that the retaining rib 224 forms a wall about the circumference of the central bore 222. In an operable position, shown in FIG. 5A, the open end 208 of the vaginal canal assembly 200 is disposed within the central bores 29 and 222 of the bottom cap 28 and the retaining plate portion 220, respectively. As shown in FIGS. 5A-5C, a stand off ring 240 is disposed about the exterior surface portion 202 of the vaginal canal assembly 200 in proximity to the open end 208. As the vaginal canal assembly 200 is moved into the operable position (FIG. 5B), the stand off ring 240 is disposed over the retaining plate portion 220 of the vaginal canal assembly 200 and the retaining rib 224 such that the stand off ring 240 and the retaining rib 224 provide a compression seal (FIG. 5A). In one embodiment, the stand off ring 240 includes an interior groove or channel 242 for receiving the retaining rib 224.

As shown in FIGS. 5B and 5C, the bracket assembly 230 is coupled to the stand off ring 240. In one embodiment, the stand off ring 240 includes internally threaded bores 244 for receiving a fastener 250 such as, for example, a screw or bolt, for securing the bracket assembly 230 to the stand off ring 240. In one embodiment, the bores 244 are through holes (e.g., the bores 244 are not internally threaded) and the fastener 250 is received by internally threaded bores (not shown) in the bottom cap 28. In one embodiment, the bracket assembly 230 includes upright portions 232 and 234.

As shown in FIGS. 5A-5C, the vaginal canal assembly 200 includes an integrally molded receiving portion, shown generally at 214, having a coupling 216 for receiving the tube 52 that delivers the fluid of interest (e.g., menses simulant) from the pump 50. The receiving portion 214 includes a passage 218 such that the fluid is provided to the interior canal 206 of the vaginal canal assembly 200 to simulate the cervical os. In one embodiment, the vaginal canal assembly 200 also includes an integrally molded support portion, shown generally at 213. The support portion 213 receives a pin 260 disposed between the upright portions 232 and 234 of the bracket assembly 230. In one embodiment, the support portion 213 is comprised of an open tubular form having a channel of a diameter to receive the pin 260. In one embodiment, the upright portions 232 and 234 include opposing slots or an opposing plurality of holes, shown generally at 236, aligned along a vertical portion of each of the uprights 232 and 234. The pin 260 is selectively positioned in opposing ones of the plurality of holes 236 along the vertical portion of the upright portions 232 and 234.

It should be appreciated that altering the vertical placement of the pin 260 along a height of the upright portions 232 and 234 influences orientation of the vaginal canal assembly 200. For example, by lowering the placement of the pin 260 within the holes 236, the vaginal canal assembly 200 pivots back about the pin 260 in a direction indicated by arrow C. In this way, an angular position of the vaginal canal assembly 200 relative to the bracket assembly 230 is adjustable. It should be appreciated that by adjusting the angular position of the vaginal canal assembly 200 relative to the bracket assembly 230 various positions of a woman (e.g., sitting, standing, lying down) is simulated. In one embodiment, the receiving portion 214 and support portion 213 are integrally formed and comprised of a same castable material as the vaginal canal assembly 200 (e.g., a RTV silicone rubber, castable polyurethane, rubber latex, plasticized PVC, and like castable materials). It should be appreciated however, that it is also within the scope of the present invention to form the receiving portion 214 and support portion 213 out of a different material.

Figure 6A:
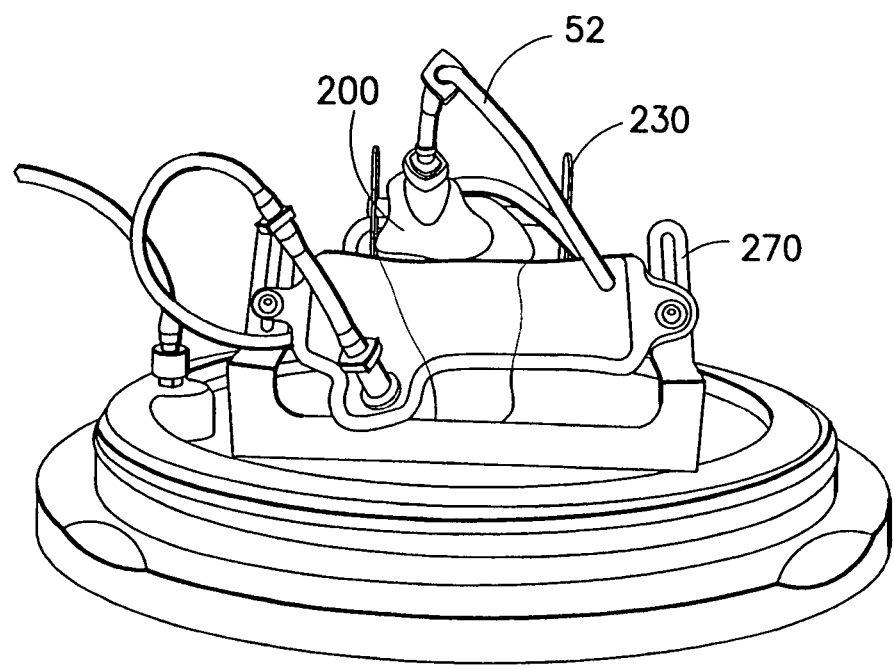
FIGS. 6A and 6B illustrate the molded vaginal canal assembly in an operable position.
Figure 6B:
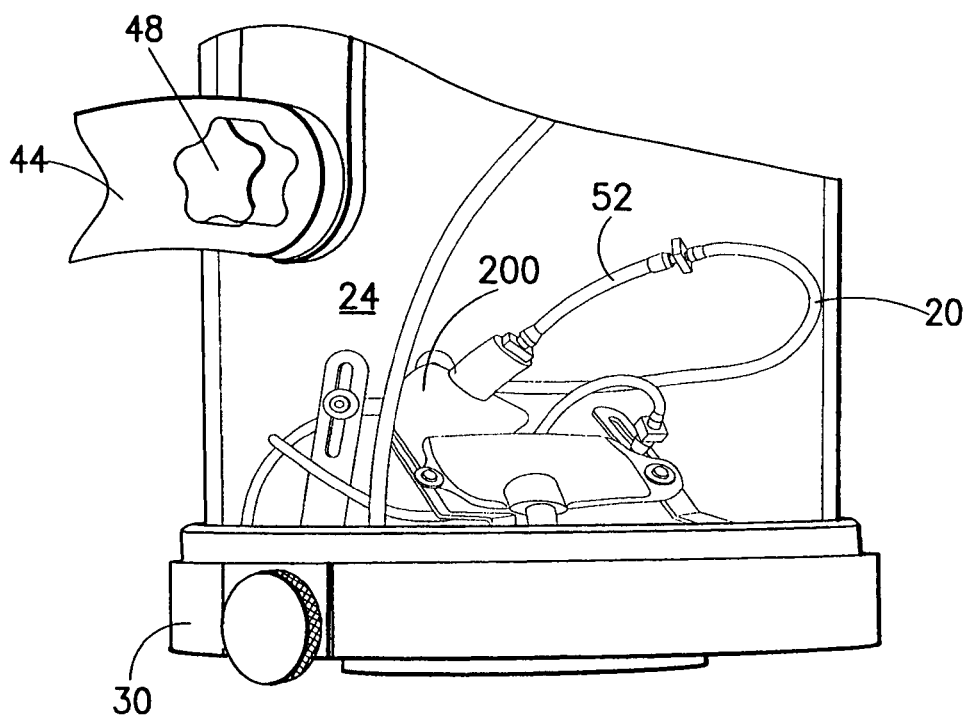
Figure 6C:
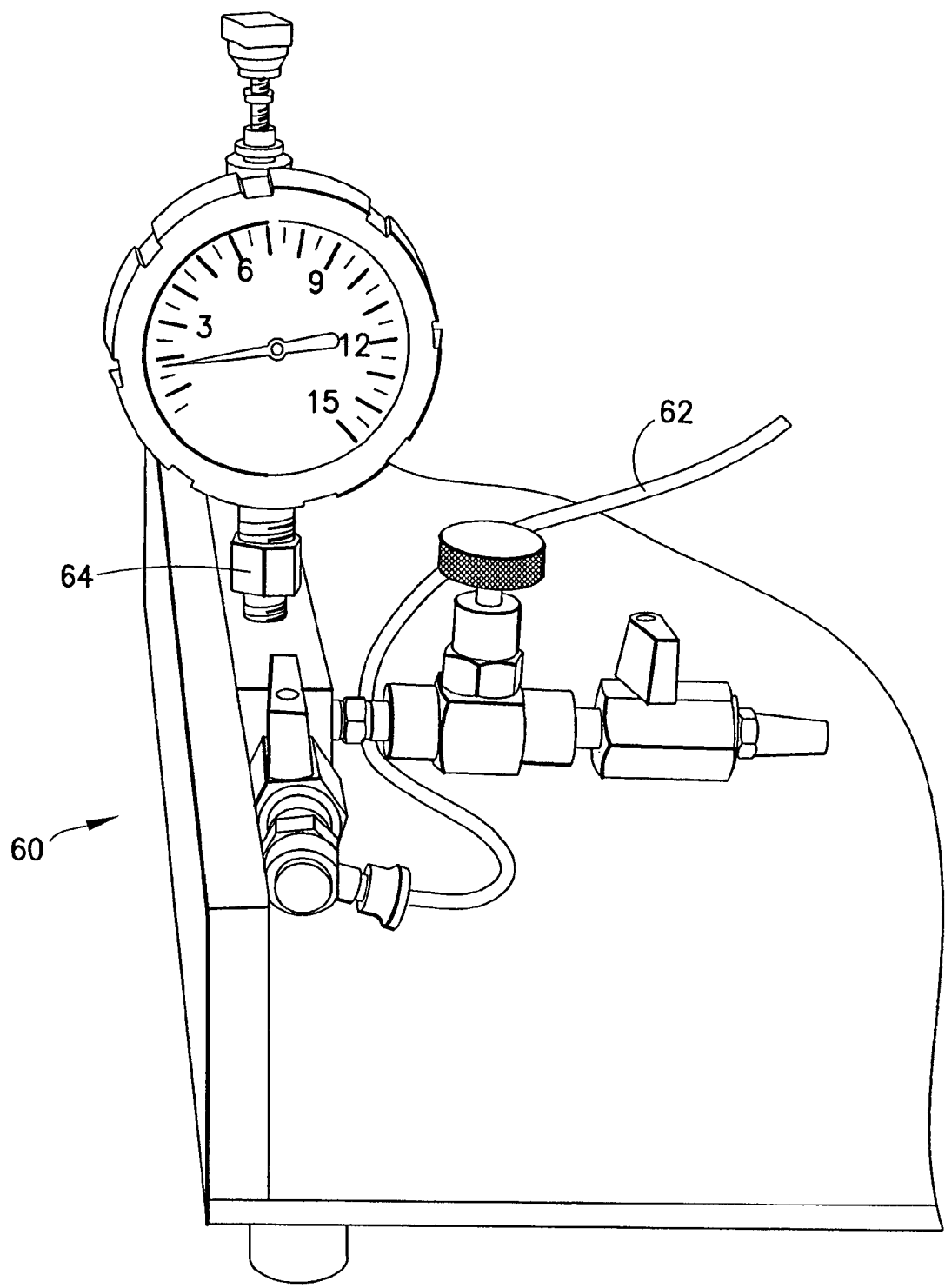
FIG. 6C illustrates a pressure regulator configured and operating in accordance with one embodiment of the present invention to provide and regulate pressure within the testing apparatus.

FIGS. 6A-6C illustrate the vaginal canal assembly 200 in the operable position coupled to the bottom cap 28 (FIG. 6A) and disposed within the pressure vessel assembly 20 (FIG. 6B). As shown in FIG. 6A, a bracket 270 is provided to support the tube 52. As described above, in the operable position, the central bore 222 of the retaining plate portion 220 of the vaginal canal assembly 200 is coaxial with the central bore 29 of the bottom cap 28 and the open end 208 of the vaginal canal assembly 200 is disposed within the central bores 29 and 222, respectively. In the operable position, a feminine hygiene product of interest (e.g., a tampon) may be disposed in the interior canal 206 of the vaginal canal assembly 200 by inserting the product into the central bore 29 of the bottom cap 28. For example, the central bore 29 of the bottom cap 28 simulates the vulva, so that inserting the product through the central bore 29 and into the interior canal 206 simulates inserting the product into the vulva and the vaginal cavity of a woman. In one embodiment, shown in FIG. 6B, a volume of the interior chamber 24 of the pressure vessel assembly 20 is filled with a liquid (e.g., water) to exert a desired pressure on the vaginal canal assembly 200. Additional pressure is applied or the pressure within the interior chamber 24 is varied via the pressure regulator 60 (FIG. 6C). As such, the vaginal canal assembly 200 and the pressure vessel assembly 20 model the human body and thus, cooperate to provide a test environment to assess the performance of the feminine hygiene product in a controlled laboratory setting (e.g., in-vitro testing).

It should be appreciated that it is within the scope of the present invention to supplement the aforementioned test environment (e.g., the pressure vessel assembly 20 and the vaginal canal assembly 200) with additional features and functions as follows. In one embodiment, a vaginal pressure sensor probe is disposed within the vaginal canal assembly 200 such that it is possible to correlate simulator performance characteristics to human subjects and/or computational models. The pressure vessel assembly 20 also includes a temperature control to selectively set, monitor and regulate a temperature in the internal chamber 24 to simulate, for example, human body vaginal cavity temperature at a desired level. Similarly, the pressure vessel assembly 20 includes a pressure control to selectively set, monitor and regulate a pressure in the internal chamber 24 such as by regulating a fluid or gel surrounding vaginal canal assembly 200. In one embodiment, one or both of the temperature and pressure controls is implemented as a programmable controller such that settings, monitoring and regulating of the temperature and/or pressure in the internal chamber 24 is performed automatically. It is also within the scope of the present invention to provide a controller operably coupled to the pump 50 for selectively controlling delivery of the menses simulant from the pump 50 to the vaginal canal assembly 200. In one embodiment, the controller is manual. In another embodiment, the controller is programmable. It should be appreciated that by controlling delivery of the menses (either manually or automatically), the present invention simulates intermittent or variable menses flow rates in the vaginal canal assembly 200.

As described above, in the human body, organs and tissues surrounding the vaginal cavity impart varying forces and pressure on the vaginal cavity that can influence performance of hygiene products disposed in the vaginal cavity. Therefore, it is desirable to simulate these forces and pressures during testing to effectively evaluate product performance. In one embodiment, anatomically correct structures surrounding the vagina cavity such as, for example, the uterus, cervix, coccyx, urinary bladder, pelvic floor, and the like, are measured, modeled and molded, e.g., using the aforementioned MRI scanning, 3-D software and 3-D mold design software, so that anatomically correct tissues and organs are included within the internal chamber 24 of the pressure vessel assembly 20 during testing. As noted above, it is within the scope of the present invention to measure, model and mold the organs and tissues surrounding the vaginal cavity for a plurality of female subjects, e.g., females of various ages (young, adult and senior) and physical sizes (short, average, and tall in height, slim, average, and heavy in weight). It is also within the scope of the present invention to employ suitable materials when forming these tissues and organ models to not only simulate anatomically correct representations, but also to provide accurate models of the tissues and organs biomechanical properties. In one embodiment, tissues comprising the pelvic floor and exterior portions of the vaginal opening of a subject female are measured, modeled and molded. The inventors have discovered that a simulation of the pelvic floor and exterior portions of the vaginal opening assist with pledget retention and provide a means for testing and evaluating tampon applicators.

In one embodiment, the pressure vessel assembly 20 includes a vibration system to simulate dynamic forces exerted on the vaginal cavity by activity of the women (e.g., walking, running, jumping, riding a bike, swimming, and like physical activity), in order to study the effect of such activity on, for example, pledget mobility and fluid retention. In one embodiment, the hygiene product is coupled to a monitor such that real-time, in simulator performance is measured. For example, a tampon pledget is coupled to a monitor such that pledget absorption is monitored in real time.

Operation of the Testing Apparatus:

The inventors have discovered that the testing apparatus 10 is particularly useful both to assess current tampon pledget designs and to assist the inventors in developing new and improved tampon designs. A method for assembling and running the testing apparatus and vaginal simulator of the present invention includes the following steps.

1. Prime and calibrate the pump 50. In a calibration process, a fluid of interest, e.g., a menses simulate, is used for calibration. In one embodiment, the menses simulant is a red standard syngyna fluid (0.9% physiological saline), housed in an appropriate vessel/reservoir (not shown) and connected by the tubing 52 to the pump 50. The flow rate of fluid driven by the pump 50 to the pressure vessel assembly 20 is tested by, for example, using a stopwatch and running the fluid into a measuring device such as, for example, a small tared beaker or graduate cylinder, for about five (5) minutes at the specified rate. A volume of the fluid is computed by multiplying the rate times five (5). If the computed versus measured volume is off more than five percent (5%), the flow rate on the pump 50 is adjusted by turning a set screw on the pump 50 to increase or decrease the rate according to a manufacturer supplied calibration chart. The flow rate test of this calibration step is repeated until the rate is within the five percent (5%) of target range.

2. Align the test apparatus 10 and, in particular, the components within the internal chamber 24 of the pressure vessel assembly 20. Determine, set and record a height of the bracket assembly 230 such that the vaginal canal assembly 200 and the bladder 80 (when attached) are at the height required for a particular experiment. Attach the two tubes 52 and 62 to the pressure vessel assembly 20, such that the tube 52 is positioned to provide the flow of the liquid fluid of interest (e.g., water, syngyna fluid or menses simulant) to the vaginal canal assembly 200 and the tube 62 is positioned to apply pressure (e.g., air flow) to the bladder 80 and/or a fluid or gel disposed within a volume of the internal chamber 24.

3. Install the simulated vagina in the test apparatus 10. Attach the vaginal canal assembly 200 to the bracket assembly 230 on an inside surface of the bottom cap 28 and couple the tube 52 from the pump 50 to the receiving portion 214 of the vaginal canal assembly 200 (as shown in FIG. 6A). Install the bottom cap 28 to the pressure vessel assembly 20 ensuring that the bottom cap 28 is secured firmly. Use the retaining clamp 32 to secure the bottom cap 28. In one embodiment, a safety bolt 33 secures the clamp 32, to ensure both safe operation and proper alignment.

4. Install the test product. Determine and record the hygiene product's (e.g., a tampon) weight and identity (e.g., features, functions and/or characteristics of the product under test). Insert the product (e.g., the tampon) into the test apparatus 10. Generally, it is preferred to use about two drops of a lubricant such as, for example, KY JELLY™ (a product of Johnson & Johnson, New Jersey, USA) to lubricate a tampon applicator in order to place the applicator in the vagina canal assembly 200 at the desired position in the interior canal 206. The record for the test should indicate whether lubrication is used or is not used. The inventors have discovered that it is preferable to use a depth gauge or other specialized ruler to determine the precise distance that the product is inserted into the interior canal 206. As noted above, placement of a tampon within the vaginal cavity of a female is one factor influencing tampon performance. Once installed, a string coupled to an end of the tampon pledget (as is generally known in the art) extends from the interior canal 206 through the open end 208 of the vaginal canal assembly 200.

5. Align the pressure vessel assembly 20 such that the internal chamber 24 is oriented straight up in a vertical position. If a particular experiment calls for the chamber 24 to be full of water, then fill the volume of the internal chamber 24 with distilled water until it reaches the resting location of the top cap 26. In one embodiment, the volume of the internal chamber 24 is approximately 9600 ml.

6. Close the pressure vessel assembly 20. Install the top cap 26 to the pressure vessel assembly 20. In one embodiment, a safety vent bolt is disposed into the top cap 26 to release pressure as needed. Attached the tube 62 from the pressure regulator 60 to an air supply. In one embodiment, the air supply is compressed air provided as a utility in the laboratory. In one embodiment, the air supply is an air cylinder coupled to the tube 62. If an air cylinder is used, it is preferable that the cylinder holds about a maximum of about thirty pounds (30 lbs).

7. While holding the pressure vessel assembly 20, loosen the locking device 48, one on each side of the assembly 20. Tilt the pressure vessel assembly 20 back in the direction of line B (FIG. 1), so that the bottom cap 28 of the pressure vessel assembly 20 is visible. In particular, the central bore 29 of the bottom cap 28 should be visible as the central bore 29 is coaxial with the interior canal 206 of the vaginal canal assembly 200 and the tampon is disposed within the interior canal 206. In the tilted position, the string of the tampon pledget is visible within the central bore 29. In one embodiment, a tilt of the pressure vessel assembly 20 is adjusted using, for example, a protractor, to an angle of interest in the particular experiment. In one embodiment, the angle of interest is typically about 30 degrees with respect to vertical (e.g., along line B of FIG. 1).

8. Set and record a desired pressure in the internal chamber 24 of the pressure vessel assembly 20 by opening the regulator 60, opening the air supply valve 64 of the air source (e.g., an air valve on a portable air supply tank). Set and record the air pressure regulator 60 to the specified value (typically about 2-3 psi, absolute). In one embodiment, an emergency relief regulator value is set to about 5 psi.

9. When the air pressure in the internal chamber 24 is at the desired value (e.g., about 2-3 psi, absolute), start the pump 50 and stopwatch simultaneously to allow fluid flow into the vaginal canal assembly 200 and, more particularly, into the interior canal 206.

10. Monitor the pressure vessel assembly 20 until tampon leakage is detected. As the pressure vessel assembly 20 is clear, monitor to see if any bypass leakage occurs around the tampon. Use a stopwatch to determine the time until leakage. The inventors have discovered that it is useful to supplement the monitoring by videotaping the experimental operation through the pressure vessel assembly 20, for subsequent review. When the first drop of fluid falls out of the testing apparatus 10 (e.g., flows out of the interior canal 206 of the vaginal canal assembly 200 and the central bore 29 of the bottom cap 28), stop the test. Turn off the pump 50 and stopwatch simultaneously. Release the pressure in the pressure vessel assembly 20, for example, the pressure in the internal chamber 24 is vented through a top air bladder in the top cap 26.

11. Evaluate the tested product. Remove, weigh and record the final weight of the tampon. Subtract the pre-test weight of the tampon (from Step 3) to determine the weight of the retained liquid and thus the tampon absorbency. Record the elapsed time to leakage and absorbency in grams. Note any unusual absorption patterns of the tampon. Also, note if it is difficult to remove from the vaginal cavity. Difficulty is pertinent in terms a measure of user comfort.

12. Reset the testing apparatus 10. After completion of a test, clean up is required. The pressure source is set off at the source. Any remaining pressure is bleed off from the internal chamber 24 and the urinary bladder 80. The pressure vessel assembly 20 is returned to the vertical, upright position. The top vent safety bolt is removed. The clamp 30 is removed from the top cap 26, the top cap 26 is removed from the body portion 22 of the pressure vessel assembly 20, and the tubing 52 and 62 is disconnected. Liquid, if any, is drained from the internal chamber 24. The vaginal canal assembly 200 is removed from the chamber 24 and inspected for any abnormalities or damage that may have occurred during the testing, e.g., a tear or the like. Once removed, the vaginal canal assembly 200 is cleaned and stored. The top cap 26 may be replaced on the body portion 22 to seal the chamber 24 during non-use and storage.

The inventive testing apparatus 10, being anatomically and biomechanically accurate, has been advantageous in evaluating overall tampon performance and, in particular, in determining tampon leakage protection characteristics.

As can be appreciated, the testing apparatus 10 is employed, in one embodiment, to test tampon pledget performance under a variety of different conditions. In particular, testing uses factorial design technology, wherein experiments are designed to study several factors at once using statistical criteria to vary the factors systematically. For example, Table 1 lists factors and conditions examined using the testing apparatus 10.

TABLE 1

| Study Factors | |
| --- | --- |
| Factors/Conditions | Typical Settings |
| Pressure | 2 psi |
| Pump Rate | 0.833 ml/min |
| Tampon Type | Prototype |

TABLE 1-continued

| Study Factors | |
| --- | --- |
| Factors/Conditions | Typical Settings |
| Tampon Size | Super unscented |
| Container Swivel Angle | 30 degrees |
| Urinary Bladder Pressure | None |
| Total DI Water Charge to Container | 9600 mls |
| Bladder Tilt | Middle |
| Bladder Horizontal Bracket | Middle |
| Vaginal Part Height | Middle |
| Top Bladder | Empty |
| Menstrual Simulant Fluid Type | Syngyna Fluid |
| Vaginal Part Lubrication | None |
| Tampon Location (use a depth gauge) | ½" past "introitus" |
| Vaginal Part Horizontal Position | Middle |

Test Results:

The following describes results demonstrated employing the testing apparatus 10 of the present invention.

| | | | | | | | | | |
| --- | --- | --- | --- | --- | --- | --- | --- | --- | --- |
| | Test 1: Effect of Varying Pump Rate | | | | | | | | |
| Test | Pump Output (g/mn) | Computed Absorbency | % Moisture LOD | Tampon Initial | Weight Final | Corrected Weight | Gram/Gram absorbency | Time to Leakage (mm:ss) | Amt of Lubrication (grams) |
| 1 | 0.292 | 6.83 | 9.17 | 2.826 | 9.655 | 2.77 | 2.47 | 25:34 | 0.232 |
| 2 | 1.668 | 6.64 | 9.17 | 2.527 | 9.163 | 2.48 | 2.68 | 4:20 | 0.282 |

Notes:
1. Vagina assembly mold of a 30 yr old subject
2. Using standard Playtex menstrual fluid
3. Pledget inserted 1 cm inside of Introitus
4. KY lube as needed
5. All adjustments to center
6. GENTLE GLIDE ™ tampon
7. KY JELLY ™ used as lubricant
8. Chamber tilt: 30 degrees
9. Top bladder, no pressure
10. Bottom bladder, no pressure
11. KY JELLY ™ applied with Q-tip
12. Using thin plastic plate with a 1" hole
13. Operator (PE)
14. Chamber water volume: 3600 mls

| | | | | | | |
| --- | --- | --- | --- | --- | --- | --- |
| | | Test 2: Comparison of Tampons of Varying Absorbency Ranges | | | | |
| Dry Weight (grams) | Wet Weight (grams) | Absorbency | Average % Moisture | Weight corrected for moisture | Gram/Gram Absorbency | Absorbency Range |
| 1.615 | 7.725 | 6.110 | 8.190 | 1.724 | 3.544 | Regular |
| 1.817 | 8.484 | 6.667 | 8.190 | 1.940 | 3.437 | Regular |
| 2.567 | 11.100 | 8.533 | 7.250 | 2.768 | 3.082 | Super |
| 2.586 | 10.824 | 8.238 | 7.250 | 2.789 | 2.954 | Super |
| 2.822 | 13.442 | 10.620 | 7.660 | 3.030 | 3.505 | Super+ |
| 3.119 | 14.372 | 11.253 | 7.660 | 3.349 | 3.360 | Super+ |

Notes:
All tampons were commercially obtained GENTLE GLIDE ™ tampons
A few drops of KY JELLY ™ applied to each tampon
Soft vagina part used
Chamber full of water
0 psi in the bottom bladder, vaginal bracket at the top, 30° tilt on chamber.
Other bracket set at mid-range
Pump flow rate target set at 2.122 grams/minute
Syngyna fluid used A statistical comparison of the data collected in Test 2 to that of FDA-mandated syngyna ranges is provided in Table 2. As the comparison illustrates, the testing apparatus 10 revealed, on average, lower absorbencies than those stated in the FDA testing regime. While lower absorbencies are measured using the inventive apparatus and testing methods, information gathered from surveys and "normal use" studies of consumers confirms that the test results obtained using the inventive apparatus and testing method reflects the information communicated in the consumer surveys. For example, normal use studies show that tampons tend to leak for women when the grams of fluid per gram of pledget is about three (3), consistent with the data from the table above. On the other hand, syngyna measurements on similar tampons give results in an about four-five (4-5) gram per gram range. Accordingly, the inventive apparatus and testing methods provide results that are in agreement with the experience of the consuming public.

TABLE 2

Comparison of Absorbency Test Results to FDA syngyna Absorbency Ranges

| Absorbency Size | Test Data | Total | FDA Absorbency Ranges |
|---|---|---|---|
| Regular | Average Absorbency | 6.39 | 6-9 grams |
|  | Average of gram/gram absorbency | 3.49 |  |
| Super | Average Absorbency | 8.39 | 9-12 grams |
|  | Average of gram/gram absorbency | 3.02 |  |
| Super Plus | Average Absorbency | 10.94 | 12-15 grams |
|  | Average of gram/gram absorbency | 3.43 |  |
|  | Pooled Standard Deviation Estimate (across all sorts) Absorbency | 0.35 |  |

As illustrated by the test results depicted in the above tables, the inventive testing apparatus 10 including the novel vaginal canal assembly 200 examines absorbency and elapsed time to leakage. Additionally, because of the flexibility of the inventive testing apparatus 10 and the vaginal canal assembly 200, the inventive apparatus and testing methods provide additional data that is difficult to get using conventional testing systems and methods. For example, and stemming from the anatomical correctness of the testing apparatus, the inventors have discovered that the results provided from the testing device 10 provide a more valuable indicator of tampon performance over a wide range of different conditions related to wearing of a tampon.

The inventors conducted additional experiments incorporating more variables than those provided in the tests and tables given above. In the additional tests, several factors were varied systematically. One notable result observed was pertaining to early bypass leakage. The inventors discovered, employing the inventive apparatus and testing method, that certain combinations of both anatomical features, tampon brands and absorbency sizes tend to result in early bypass leakage, for example, the tampon begins to leak almost right after the experiment starts. After a period of time, a bottom portion of the tampon expands and bypass leakage is stopped until the tampon is fully saturated with liquid. Tables 3A and 3B depict the factors and results observed in the additional tests.

TABLE 3A

Factors Evaluated

| | | Experimental Sequence No. | | | | | | |
|---|---|---|---|---|---|---|---|---|
| | | 1 | 2 | 3 | 4 | 5 | 6 | 7 |
| Factors | Pump Rate, grams/min | 0.98 | 0.98 | 0.98 | 0.98 | 0.98 | 0.98 | 0.29 |
| | Tampon Brand | Gentle Glide | Beyond | Gentle Glide | Gentle Glide | Gentle Glide | Beyond | Gentle Glide |
| | Tampon Size | Regular | Super+ | Super+ | Super+ | Super+ | Super+ | Super+ |
| | Tampon location/ displacement | 1 cm in | All the way up and left | All the way up & left | 1 cm in | 1 cm in | All the way up & left | 1 cm in |
| | Chamber tilt angle | 0 angle, vertical | 0 angle, vertical | 0 angle, vertical | 0 angle, vertical | 0 angle, vertical | 45 deg angle | 45 deg angle |
| | Water added to chamber | empty | empty | full | full | Empty | empty | Empty |
| | Bladder bracket location | bladder lowest | bladder highest | bladder lowest | bladder lowest | bladder lowest | bladder highest | bladder highest |
| | Bladder pressure (hand pump) | Full | none | full | none | None | full | None |
| | Top pressure Bracket for Vagina Assy | 3 psig highest | 0 psig lowest | 3 psig highest | 0 psig lowest | 0 psig Lowest | 3 psig highest | 0 psig lowest |

TABLE 3B

Results Observed

| | | Experimental Sequence No. | | | | | | |
|---|---|---|---|---|---|---|---|---|
| | | 1 | 2 | 3 | 4 | 5 | 6 | 7 |
| Results | Initial Pledget Weight (grams) | 1.35 | 3.36 | 3.37 | 3.84 | 3.60 | 3.37 | 3.46 |
| | Final Pledget Weight (grams) | 6.56 | 12.20 | 14.17 | 14.91 | 14.36 | 11.89 | 14.08 |
| | Early bypass leakage | No | No | No | No | No | No | No |
| | Absolute Absorbency | 5.21 | 8.84 | 10.80 | 11.07 | 10.76 | 8.52 | 10.62 |
| | Gram/Gram Absorbency | 3.86 | 2.63 | 3.20 | 2.88 | 2.99 | 2.53 | 3.07 |
| | Elapsed time | 5.18 | 9.00 | 11.18 | 11.92 | 11.95 | 10.08 | 34.40 |
| | Comments | Soaked up quickly | Absorbed alot | Bladder pushed on canal | No pressure anywhere | Slow absorbtion, held a lot of fluid | none | Very slow and long |

TABLE 4

Observations regarding Tampon Size and Location versus Bypass Leakage.

| | | Tampon Location | |
|---|---|---|---|
| Tampon Size | Data | 1 cm in | All the way up and to left |
| Regular | Count (Number of Experiments) | 34 | 36 |
| | Sum of Bypass (Number of Occurrences) | 0 | 5 |
| Super Plus | Count (Number of Experiments) | 33 | 31 |
| | Sum of Bypass (Number of Occurrences) | 0 | 0 |
| | Total Number of Experiments: | 134 | |

As shown in Table 4, the inventors observed five (5) instances of bypass leakage in a total of 134 experiments. Each of the five instances occurred in Regular size tampons placed up very high in the vaginal fornix. No other instances of bypass leakage was observed for the other experiments. It should be appreciated that the observed results are not expected on statistical grounds. However, the experiments do reflect what consumers have communicated in focus groups as well as results obtained in MRI studies. Accordingly, the inventive apparatus and testing methods provide results consistent with that obtained from consumers and that today, have not been verified using conventional in laboratory testing, namely, that consumers who use low absorbency tampons often place them up too high in the vaginal cavity and thus experience early bypass leakage.

Although described in the context of preferred embodiments, it should be realized that a number of modifications to these teachings may occur to one skilled in the art. Accordingly, it will be understood by those skilled in the art that changes in form and details may be made therein without departing from the scope and spirit of the invention.

What is claimed is:

1. An apparatus for in-vitro testing of a feminine hygiene product, comprising:
 a body having an internal chamber, the body including a bottom surface having a central bore open to the internal chamber;
 a pump coupled to the body, the pump providing a fluid of interest;
 a vaginal canal assembly disposed within the internal chamber, the vaginal canal assembly including: a wall defining an interior canal, the interior canal having an open end and a closed end, the open end of the interior canal being coaxial writhe central bore, the interior canal accepting the feminine hygiene product; and a passage in the wall for providing the fluid of interest to the interior canal;
 a bracket assembly disposed within the internal chamber, the bracket assembly having upright portions, the upright portions accepting the vaginal canal assembly and retaining the vaginal canal assembly at a predetermined orientation within the internal chamber; and
 wherein the bracket assembly further includes: a pin; and the upright portions include a plurality of opposing bores aligned along a vertical portion of the upright portions, the opposing bores accepting the pin wherein the pin is positioned within corresponding opposing bores for selectively adjusting the orientation of the vaginal canal assembly.

2. The apparatus of claim 1, wherein the vaginal canal assembly further includes a retaining plate portion, and wherein when the vaginal canal assembly is disposed in the body the retaining plate portion seals the central bore.

3. The apparatus of claim 2, further including: a pressure regulator coupling the body to an air supply; wherein the pressure regulator controls pressure exerted on the vaginal canal assembly from a volume of air within the internal chamber.

4. The apparatus of claim 2, further including: a retaining ring disposed about an external surface of the vaginal canal assembly, the retaining ring and retaining plate portion of the vaginal canal assembly cooperating to seal the central bore of the body.

5. The apparatus of claim 1, further including a stand supporting the body, the stand comprising: a retaining device for rotational and angular coupling of the body to the stand; and a locking device cooperating with the retaining device for selectively securing the body in at least one of a rotational position and an angular position.

6. The apparatus of claim 1, wherein the pump is comprised of a variable rate metering pump.

7. The apparatus of claim 6, further including: a control coupled to the pump, the control controlling delivery of the fluid for simulating at least one of intermittent and variable flow rates in the vaginal canal assembly.

8. The apparatus of claim 1, wherein the fluid is one of water, syngyna fluid and a menses simulant.

9. The apparatus of claim 1, wherein the vaginal canal assembly further includes a support portion accepting the pin of the bracket assembly, and wherein a location of the pin within the plurality of opposing bores adjusts an angular orientation of the vaginal canal assembly within the body.

10. The apparatus of claim 1, further including: a bladder disposed in the chamber in proximity to the vaginal canal assembly, the bladder exerting a force on the vaginal canal assembly.

11. The apparatus of claim 1, wherein the body is comprised of a clear polycarbonate such that the internal chamber is visible.

12. The apparatus of claim 1, wherein the vaginal canal assembly is comprised of at least one material selected from the group consisting of silicone rubber, castable polyurethane, rubber latex, plasticized PVC, and any combinations thereof for simulating biomechanical properties of a human female's vaginal cavity.

13. An apparatus for in-vitro testing of a feminine hygiene product, comprising: a pressure vessel assembly including: a body portion having an internal chamber; and a bottom cap removably coupled to the body portion, the bottom cap having a central bore; a pump coupled to the pressure vessel assembly, the pump providing a fluid of interest to the pressure vessel assembly; a vaginal canal assembly disposed within the internal chamber of the pressure vessel assembly, the vaginal canal assembly including: a wall defining an interior canal, the interior canal having an open end and a closed end, the open end coaxial with the central bore of the bottom cap, the interior canal accepting the feminine hygiene product; a passage for providing the fluid of interest to the interior canal; and a support portion; a bracket assembly disposed within the internal chamber, the bracket assembly having upright portions, the upright portions accepting the support portion of the vaginal canal assembly and selectively retaining the vaginal canal assembly in one of a plurality of angular orientations.

14. The apparatus of claim 13, wherein the vaginal canal assembly further includes a retaining plate portion and wherein when the vaginal canal assembly is disposed in the internal chamber, the retaining plate portion seals the central bore of the bottom cap.

15. The apparatus of claim 14, further including: a pressure regulator coupling the pressure vessel assembly to an air supply; wherein the pressure regulator controls pressure exerted on the vaginal canal assembly from a volume of air within the internal chamber.

* * * * *